(12) United States Patent
Sun et al.

(10) Patent No.: US 7,024,770 B2
(45) Date of Patent: Apr. 11, 2006

(54) METHOD OF MAKING A DENTAL PRODUCT

(75) Inventors: Benjamin J. Sun, York, PA (US); Andrew M. Lichkus, York, PA (US)

(73) Assignee: Dentsply Research & Development Corp., Los Angeles, CA (US)

( * ) Notice: Subject to any disclaimer, the term of this patent is extended or adjusted under 35 U.S.C. 154(b) by 438 days.

(21) Appl. No.: 10/431,712

(22) Filed: May 8, 2003

(65) Prior Publication Data

US 2003/0190585 A1    Oct. 9, 2003

Related U.S. Application Data

(63) Continuation of application No. 09/682,440, filed on Sep. 4, 2001, now Pat. No. 6,592,369.

(51) Int. Cl.
*A61C 5/10* (2006.01)

(52) U.S. Cl. ............ 29/896.1; 433/167; 523/115

(58) Field of Classification Search .......... 29/896.1; 433/167, 199.1; 523/109, 115, 116
See application file for complete search history.

(56) References Cited

U.S. PATENT DOCUMENTS

| | | | |
|---|---|---|---|
| 4,017,971 A | 4/1977 | Hazar | 32/2 |
| 4,094,067 A | 6/1978 | Hazar | 32/2 |
| 4,097,992 A | 7/1978 | Hazar | 32/2 |
| 4,133,110 A | 1/1979 | Bernstein et al. | 32/2 |
| 4,161,065 A | 7/1979 | Gigante | 32/2 |
| 4,175,322 A | 11/1979 | Tureaud | 433/171 |
| 4,247,287 A | 1/1981 | Gigante | 433/199 |
| 4,248,807 A | 2/1981 | Gigante | 264/18 |
| 4,259,074 A | 3/1981 | Link | 433/214 |
| 4,267,133 A | 5/1981 | Kohmura et al. | 264/18 |
| 4,345,900 A | 8/1982 | Katz et al. | 433/171 |
| 4,375,966 A | 3/1983 | Freeman | 433/37 |
| 4,398,007 A | 8/1983 | Kubota et al. | 526/273 |
| 4,457,818 A | 7/1984 | Denyer et al. | 204/159 |
| 4,543,063 A | 9/1985 | Cohen | 433/175 |
| 4,551,098 A | 11/1985 | Blair | 433/171 |
| 4,609,351 A | 9/1986 | Blair | 433/55 |
| 4,705,476 A | 11/1987 | Blair | 433/171 |
| 4,711,913 A | 12/1987 | Tateosian et al. | 522/14 |
| 4,721,735 A | 1/1988 | Bennett et al. | 522/71 |
| 4,740,245 A | 4/1988 | Futami et al. | 106/35 |
| 4,813,875 A | 3/1989 | Hare | 433/214 |
| 4,978,298 A | 12/1990 | Eliasz | 433/213 |
| 5,037,473 A | 8/1991 | Antonucci et al. | 106/35 |
| 5,063,255 A | 11/1991 | Hasegawa et al. | 522/96 |
| 5,177,120 A | 1/1993 | Hare et al. | 433/37 |
| 5,213,498 A | 5/1993 | Pelerin | 433/37 |
| 5,304,063 A | 4/1994 | Ginsburg | 433/199 |
| 5,403,186 A | 4/1995 | Ginsburg | 433/199 |
| 5,431,563 A | 7/1995 | Huybrechts | 433/48 |
| 5,591,786 A | 1/1997 | Oxman et al. | 533/109 |
| 5,635,545 A | 6/1997 | Oxman et al. | 523/115 |
| 5,711,668 A | 1/1998 | Huestis | 433/167 |
| 5,993,208 A | 11/1999 | Jonjic | 433/50 |
| 6,031,015 A | 2/2000 | Ritter et al. | 522/77 |
| 6,057,383 A | 5/2000 | Volkel et al. | 523/116 |
| 6,127,449 A | 10/2000 | Bissinger et al. | 523/109 |

FOREIGN PATENT DOCUMENTS

EP    0 630 640    12/1994

OTHER PUBLICATIONS

Moszner et al; Synthesis, characterization and polymerization of waxy monomers; Die Angewandte Makromolekulare 245 (1997) 155-164, (Nr. 4283).

*Primary Examiner*—Todd E. Manahan
(74) *Attorney, Agent, or Firm*—Daniel W. Sullivan; James B. Bieber; Douglas J. Hura

(57) ABSTRACT

The invention provides high strength dental polymeric dental products made from wax-like polymerizable dental material. These dental products have superior strength compared to products formed from prior wax-like polymerizable materials. Prior wax-like polymerizable materials do not form strong enough polymeric material for making dentures. High strength dentures are made by positioning artificial teeth in wax-like polymerizable dental material of the invention. This material is then shaped and polymerized to the form a denture base of high strength dental polymeric material. These dentures are completed without forming wax and without applying inorganic plaster to the artificial teeth.

16 Claims, No Drawings

METHOD OF MAKING A DENTAL PRODUCT

This application is a continuation of application Ser. No. 09/682,440, filed Sep. 4, 2001 now U.S. Pat. No. 6,592,369.

DETAILED DESCRIPTION

The invention relates to wax-like polymerizable materials. The invention provides wax-like polymerizable dental materials, and methods of forming dental products of high strength dental polymeric material. This wax-like polymerizable dental material is quickly and easily reshaped. It is reshaped by warming, and shaping while warm and then allowing it to cool to room temperature. The shaped wax-like polymerizable dental material is cured to form dental products. These dental products have superior strength compared to products formed from prior wax-like polymerizable materials. Prior wax-like polymerizable materials do not form strong enough polymeric material for making dentures. High strength dentures are made by positioning artificial teeth in wax-like polymerizable dental material of the invention. The disclosures of U.S. patent application Ser. No. 09/670,364 filed Sep. 26, 2000 and U.S. provisional patent application Ser. No. 06/237,523 filed Oct. 4, 2000 are incorporated herein by reference in their entirety.

Volkel et al in U.S. Pat. No. 6,057,383 (and Canadian Patent Application 2207351), assigned to Ivoclar, disclose wax-like polymerizable material for making entire dental products. The prior art does not disclose a wax-like polymerizable material for forming dentures or other high strength products.

The invention provides a high strength dental polymeric material formed from wax-like polymerizable dental material. High strength dental polymeric dental products include partial dentures and full dentures.

Working wax-like polymerizable dental material, often includes molding, shaping, and/or carving. When heated, wax-like polymerizable dental material softens. In its softened state, it is believed to be partially crystalline and have a flowable amorphous phase, which allows some flowability of the material. Preferably, wax-like polymerizable dental material is dimensionally stable below 24° C. and softened at and above 24° C. More preferably it is softened at and above 30° C. By heating from its dimensionally stable condition, wax-like polymerizable dental material of the invention undergoes a rapid transition to being freely flowable. By cooling from its softened state, wax-like polymerizable dental material of the invention undergoes a rapid transition to being dimensionally stable. Small volumes of wax-like polymerizable dental material may be worked, while being warmed on the dental device. They may be dispensed from a heated syringe-type dispensing device, spatula, electric spatula, disposal dropper or other mechanical or electrical dispenser. To make a denture, wax-like polymerizable dental material is positioned on a polymeric base plate made from an impression of a patient's mouth. Artificial teeth are positioned in the wax-like polymerizable dental material, which is then shaped by melting and resolidifying. Then the wax-like polymerizable dental material is polymerized to form a denture. Thus the denture is formed without applying inorganic plaster to the artificial teeth and without positioning artificial teeth in a mold as required by conventional lost wax or other similar prior art methods of forming a denture. Compounds, which are readily partially crystallizable and useful in wax-like polymerizable dental material of a preferred embodiment of the invention, include methacrylate (or acrylate) compounds prepared for example by reaction of a urethane pre-oligomer with hydroxyalkymethacrylate. Preferably such compounds have a structure within the scope of one of general formulas I–V below. Preferably the urethane pre-oligomer is linear, comprises isocyanate end groups and has a structure within the scope of general formula I:

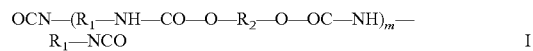

wherein $R_1$ and $R_2$ are either an alkyl having from 1 to 14 carbon atoms or containing at least an aromatic group having from 6 to 14 carbon atoms, m is an integer from 0 to 20, the value of m in the oligomer depends on the molar ratio of diisocyanate to diol used, and the value of m increases as this molar ratio decreases. The diisocyanate portion has the structure OCN—$R_1$—NCO and the diol portion has the structure HO—$R_2$—OH.

Alternatively, urethane pre-oligomer is formed by reaction of at least one diol with excess, at least one diisocyanate to yield a urethane pre-oligomer having a structure within the scope of one or more of general formulas: II–IV

[t3]

| General Formulas:II–IV | |
|---|---|
| OCN—($R_1$—NH—CO—O—$R_2$—O—OC—NH)$_m$—($R_1$—NH—CO—O—$R'_2$—O—OC—NH)$_n$—$R_1$—NCO | II |
| OCN—($R_1$—NH—CO—O—$R_2$—O—OC—NH)$_m$—($R''_1$—NH—CO—O—$R_2$—O—OC—NH)$_n$—$R'_1$—NCO | III |
| OCN—($R_1$—NH—CO—O—$R_2$—O—OC—NH)$_m$—($R''_1$—NH—CO—O—$R'_2$—O—OC—NH)$_n$—$R'_1$—NCO | IV | wherein $R_1$, $R'_1$, $R_2$ and $R'_2$ each independently is an alkyl having from 1 to 14 carbon atoms or at least an aromatic group having from 6 to 14 carbon atoms, n and m are each independently integers from 0 to 20, the sum of n and m in the oligomer depends on the molar ratio of diisocyanates to diols used, and the value of the sum of n and m increases as this molar ratio decreases. The diisocyanates have the structures OCN—$R_1$—NCO and OCN—$R'_1$—NCO and the diols have the structures HO—$R_2$—OH and HO—$R'_2$—OH. The more complex structures of urethane pre-oligomer are constructed from at least two different diols and at least two different diisocyanates.

Reaction of the urethane pre-oligomer with the ethylenically unsaturated monomer as defined below yields a polymerizable compound having the structure within the scope of the general formula V:$CH_2$=$C(R_3)$—$CO_2$—$R_4$—CO—NH—($R_1$—NH—CO—O—$R_2$—O—OC—NH)$_n$—$R_1$—NH—CO—$R_4$—$O_2$C—$C(R_3)$=$CH_2$V wherein $R_3$ is hydrogen, or an alkyl, such as a methyl group, and $R_4$ is an alkyl group having from 1 to 14 carbon atoms, and n is an integer from 0 to 20. The typical ethylenically unsaturated monomer is a hydroxyalkyl (meth) acrylate, e.g. 2-hydroxyethyl methacrylate, hydroxypropyl methacrylate, caprolactone 2-(methacryloyloxy) ethyl ester, etc.

Preferred mechanical properties of cured resin and the adequate handling properties of compositions, polymerizable compound, are present when the value of n in the compound is not greater than 10; more preferably n is not greater than 5. The preferred value of n in the compound largely depends on the requirements of the specific application. The most preferable value of n in the compound for aromatic ring based diol is between 1 and 3. Therefore, the molar ratio of diisocyanate to diol for aromatic ring based diol is most preferable between 1.33 and 2. The most preferable value of n in the compound for alkyl based diol is between 1 and 4. Therefore, the molar ratio of diisocyanate to diol for alkyl based diol is most preferable between 1.25 and 2.

Catalysts known in the art may be used to accelerate the formation of the isocyanate-ended pre-oligomer and end-capped ethylenically unsaturated monomer, for examples, tertiary amines and metal salts, e.g. stannous octoate and in particular dibutyl tin dilaurate. Preferred stabilizers used in this invention are butylated hydroxytoluene (BHT) and the methyl ether of hydroquinone (MEHQ).

Preferably compounds of the invention are difunctional methacrylates including reaction products of bisphenol A propoxylate, 1,6-diisocyanatohexane and 2-hydroxyethyl methacrylate, reaction products of bisphenol A propoxylate, trimethyl-1,6-diisocyanatohexane and 2-hydroxyethyl methacrylate, a series of reaction products of bisphenol A, trimethyl-1,6-diisocyanatohexane and 2-hydroxylethyl methacrylate, a series of reaction products of bisphenol A, 1,6-diisocyanatohexane and 2-hydroxylethyl methacrylate, a series of reaction products of trimethyl-1,6-diisocyanatohexane, 2,5-dimethyl-2,5-hexanediol and 2-hydroxyethyl methacrylate, a series of reaction products of trimethyl-1,6-diisocyanatohexane, 1,6-diisocyanatohexane, 2,5-dimethyl-2,5-hexanediol and 2-hydroxyethyl methacrylate, a series of reaction products of trimethyl-1,6-diisocyanatohexane, 1,6-diisocyanatohexane, bisphenol A propoxylate and 2-hydroxyethyl methacrylate, caprolactone 2-(methacryloyloxy) ethyl ester, and derivatives of above compounds.

Diisocyanates useful for making wax-like polymerizable dental material of the invention include trimethyl-1,6-diisocyanatohexane, 1,6-diisocyanatohexane, 1,8-diisocyanatooctane, isophorone diisocyanate, 4.4"-methylenebis(cyclohexyl isocyanate), cyclohexyl diisocyanate, 3-methylhexane-1,6-diisocyanate, 3-ethyl-1,6-hexanediisocyanate, 5-methyl-1,9-nonanediisocyanate, 5-ethyl-1,10-decanediisocyanate, 2,3-dimethyl-1,6-hexanediisocyanate, 2,4-dimethyl-1,8-octanediisocyanate, 2,4,6-trimethyl-1,7-heptanediisocyanate, 2,3-dimethyl-5-ethyl-1,8-octanediisocyanate, 2-methyl-4,6,8,10-tetrapropyl-1,12-dodecanediisocyanate and the like, and mixtures thereof. Examples of diisocyanates that are also suitable include aromatic diisocyanates, for example, 4,4-methylene bis(phenyl isocyanate), 2,4-tolylene diisocyanate, 2,6-tolylene diisocyanate, 1,4-phenyl diisocyanate, 1,5-naphthalene diisocyanate, 1,3-bis (isocyanatomethyl)benzene, 1,3-bis(isocyanato-1-methylethyl)benzene, 1,3-bis(isocyanatomethyl)cyclohexane, 3,3"-bitoluene diisocyanate, 1,4-xylylene diisocyanate and the like, and mixtures thereof.

Examples of diols useful for making compounds for wax-like polymerizable dental material of the invention include 1,4-butanediol, 1,6-hexanediol, 1,10-decanediol, 1,9-decanediol, 1,12-dodecanediol, 1,14-tetradecanediol, 2,5-dimethyl-2,5-hexanediol, hydrogenated bisphenol A, bisphenol A, propoxylated bisphenol A, ethoxylated bisphenol A, bis (2-hydroxyethyl)terepthalate, and mixtures thereof.

Examples of methacrylates (or acrylates) useful for making compounds for wax-like polymerizable dental material of the invention include 2-hydroxyethyl methacrylate, 2-hydroxyethyl acrylate, 2-hydroxypropyl methacrylate, 3-hydroxypropyl methacrylate, hydroxypropyl acrylate, glycerol dimethacrylate, glycerolmonomethacrylate, 2-hydroxyethyl acrylate, hydroxypropyl acrylate, 4-hydroxybutyl methacrylate, 4-hydroxybutyl acrylate, 2-hydroxy-3-phenoxypropyl acrylate, 2-hydroxycyclohexyl methacrylate, caprolactone 2-(methacryloyloxy)ethyl ester, pentaerythritol triacrylate, 2-hydroxycyclohexyl acrylate and mixture thereof.

Wax-like polymerizable dental material may include one or more initiating systems to cause them to harden promptly. Light curable wax-like polymerizable dental materials preferably include a light sensitizer, for example camphorquinone, Lucirin TPO, or methyl benzoin which causes polymerization to be initiated upon exposure to activating wavelengths of light; and/or a reducing compound, for example tertiary amine.

A room temperature or heat activating catalyst system is preferably included in the wax-like polymerizable dental material of the invention. Preferably included is a peroxide capable of producing free radicals when activated by a reducing agent at room temperature or by heating. Preferred peroxides include benzyl peroxide and lauroyl peroxide.

Wax-like polymerizable dental materials of the invention are believed to rapidly partially recrystallize. This rapid recrystallizability provides a unique combination of free flowability and dimensional stability, depending on its temperature. It is believed that the material rapidly transitions from a freely flowable state by means of rapid crystallization to a dimensionally stable state. The material at solidification temperatures is partially crystalline and the crystallinity present in an amorphous phase results in the effective dimensional stability of the material. "Crystallinity" as used herein refers to regularity and order within a material resulting in a heat of fusion of at least 1.0 J/g at and below 50° C. Heat of Fusion as used herein refers to enthalpy of fusion as determined by ASTM 793-95. Percent crystallinity is determined by measuring the heat of fusion using differential scanning calorimetry according to ASTM test method E 793-95.

The wax-like polymerizable dental material of the invention is useful for formation of dental products including full dentures, partial dentures, denture liners, custom trays, artificial teeth, repairs for natural teeth, veneers, denture repairs, denture reline, night guards, splints, retainers, orthodontic components, crowns, bridges, provisional dental devices, inlays, onlays, and tooth restorative fillings, orthodontic appliances, oral orthopedic appliances, temporary dentures, temporary partial dentures; maxillofacial prostheses, obturators, and occular prostheses.

Compositions in accordance with the invention may further include fillers, pigments, stabilizers, plasticizers and fibers. Preferably, polymerizable dental compositions in accordance with the invention include from about 2 to about 95 percent by weight filler particles. More preferably, these compositions include from about 10 to about 85 percent by weight filler. Nanocomposites and ceramers may be formed from these composites. The fillers preferably include both organic and inorganic particulate fillers to further reduce polymerization shrinkage, improve wear resistance and modify the mechanical and physical properties.

A preferred embodiment of the invention provides a high strength dental polymeric material formed by light curing wax-like polymerizable dental material shaped into at least a portion of a denture base. Preferably the wax-like polymerizable dental material has a flexural modulus of at least 400,000 psi and a flexural strength of at least 7,000 psi and an un-notched impact strength of at least 2 foot-pounds/inch. Preferably the denture comprises denture base, and a tooth comprising an interpenetrating polymer network polymeric matrix and at least 0.1 percent by weight of self-lubricating particles having a particle size less than 500 microns effectively bonded to and distributed in the polymeric matrix.

Preferably the bond strength between the tooth and the denture base is at least 4,480 psi.

"Wax-like" as used herein refers to material which is flowable (fluid) above 40° C., and becomes dimensionally stable (solidifies: i.e. is nonfluid) at least at and below 23° C., within 5 minutes. Thus, wax-like material is flowable when it is at and above 40° C., and becomes dimensionally stable when it is at and below 23° C. Flowable wax-like material having a temperature from 100° C. to 40° C., becomes dimensionally stable within 5 minutes by cooling by exposure to an ambient temperature between 23° C. and 0° C. Flowable wax-like material having a temperature from 100° C. to 40° C., becomes dimensionally stable within (in order of increasing preference) 2, 1, 0.5 or 0.3 minutes by cooling by exposure to an ambient temperature between 23° C. and 0° C.

"High strength dental polymeric material" as used herein refers to material having a polymeric matrix having a flexural modulus of at least 250,000 psi and a flexural strength of at least 5,000 psi. Optionally, high strength dental polymeric material includes reenforcing filler. However, the polymeric matrix alone (without any reenforcing filler) has a flexural modulus of at least 250,000 psi and a flexural strength of at least 5,000 psi. Preferably high strength dental polymeric material has a polymeric matrix having a flexural modulus of at least 300,000 psi and a flexural strength of at least 7,000 psi, and an un-notched impact strength of at least 2 foot-pounds/inch$^2$. More preferably high strength dental polymeric material in order of increasing preference has a polymeric matrix having a flexural modulus of at least 350,000 psi and a flexural strength of at least 12,000 psi, and an un-notched impact strength of at least 3.0 foot-pounds/inch. High strength dental polymeric material is preferably formed into dental products including full dentures, partial dentures, denture relines, night guards, crowns and bridges by polymerization of wax-like polymerizable dental material.

"Flexural strength, and flexural modulus" as used herein refers to results of testing according to ASTM D790 (1997). "Notched impact strength" as used herein is also referred to as "notched Izod impact resistance" and refers to results of testing according to ASTM D256 (1997). "Un-notched impact strength" as used herein refers to results of testing according to ASTM D4812 (1993).

In the following examples, unless otherwise indicated, all parts and percentages are by weight; Lucirin TPO refers to 2,4,6-trimethylbenzoyldiphenylphosphine oxide made by BASF, and the visible light curing unit used was a TRIAD VLC visible light curing unit modified by adding a fifth light to provide about 30 milliwatts/cm$^2$ of from 350 to 450 nm light.

EXAMPLE 1

Preparation of Oligomer

A reactor was charged with 1176 grams of trimethyl-1,6-diisocyanatohexane (5.59 mol) and 1064 grams of bisphenol A propoxylate (3.09 mol) under dry nitrogen flow and heated to about 65° C. under a positive nitrogen pressure. To this reaction mixture, 10 drops of catalyst dibutyltin dilaurate were added. The temperature of the reaction mixture was maintained between 65° C. and 140° C. for about 70 minutes and followed by additional 10 drops of catalyst dibutyltin dilaurate. A viscous paste like isocyanate end-capped intermediate product was formed and stirred for 100 minutes. To this intermediate product, 662 grams (5.09 mol) of 2-hydroxyethyl methacrylate and 7.0 grams of BHT as an inhibitor were added over a period of 70 minutes while the reaction temperature was maintained between 68° C. and 90° C. After about five hours stirring under 70° C., the heat was turned off, and oligomer was collected from the reactor as semi-translucent flexible solid and stored in a dry atmosphere.

EXAMPLE 2

Preparation of Monomer

A reaction flask was charged with 700 grams of 1,6-diisocyanatohexane and heated to about 70° C. under a positive nitrogen pressure. To this reactor were added 1027 grams of 2-hydroxyethyl methacrylate, 0.75 gram of catalyst dibutyltin dilaurate and 4.5 grams of butylated hydroxy toluene (BHT). The addition was slow and under dry nitrogen flow over a period of two hours. The temperature of the reaction mixture was maintained between 70° C. and 90° C. for another two hours and followed by the addition of 8.5 grams of purified water. One hour later, the reaction product was discharged as clear liquid into plastic containers and cooled to form a white solid and stored in a dry atmosphere.

EXAMPLE 3

Preparation of Polymerizable Denture Contour Material

A wax-like polymerizable dental material was prepared by stirring at 85° C. a liquid mixture of 63.0 grams of oligomer made the procedure of Example 1 and 37.0 grams of compound of Example 2. 0.35 gram of 2,4,6-trimethyl-benzoyldiphenylphosphine oxide, (Lucirin TPO made by BASF), 0.5 gram of solution containing 8.3% camphorquinone (CQ), 25% ethyl 4-dimethylaminobenzoate (EDAB) and 66.7% 1,6-hexanediol dimethacrylate (HDDMA).

EXAMPLE 4

Preparation of Polymerizable Denture Base Plate (or Reline) Material

A light curable polymerizable material was prepared by stirring at 85° C. a liquid of 98.0 grams of TBDMA oligomer of Example 1, 0.35 gram of 2,4,6-trimethylbenzoyldiphenylphosphine oxide, (Lucirin TPO made by BASF), 1.5 gram of solution containing 8.3% camphorquinone (CQ), 25% ethyl 4-dimethylaminobenzoate (EDAB) and 66.7% 1,6-hexanediol dimethacrylate (HDDMA), 0.1 gram of red acetate fibers and 0.05 gram of pigment.

EXAMPLE 5

Preparation of Polymerizable Wax-Like Denture Contour Material

A light curable wax-like polymerizable dental material was prepared by stirring at 85° C. a liquid mixture of 50.5 grams of oligomer of Example 1, 45.0 grams of monomer of Example 2 and 4.0 grams of stearyl acrylate from Sartomer. To this mixture were added 0.35 gram of 2,4,6-trimethyl-benzoyldiphenylphosphine oxide (Lucirin TPO), 0.1 gram of red acetate fibers and 0.05 gram of pigment concentrates. The polymerizable wax-like material formed becomes flowable at 65 to 68° C.

EXAMPLE 6

Preparation of Polymerizable Denture Set-Up Material

A light curable polymerizable material was prepared by stirring at 85° C. a liquid mixture of 84.5 grams of oligomer of Example 1 and 15.0 grams of monomer of Example 2. To this mixture, 0.35 gram of 2,4,6-trimethylbenzoyldiphenylphosphine oxide (Lucirin TPO), 0.1 gram of red acetate fibers and 0.05 gram of pigment were added.

EXAMPLE 7

Preparation of a Denture without Forming a Mold Cavity of a Denture Base

A plaster cast of a patient's mouth is coated with a release agent (e.g., Al-Cote and Isolant sold by Dentsply International Inc. or Teflon solution such as Krytox from Dupont) and heated to 55° C. in an incubator. An arch-shaped baseplate resin containing 14 grams of the product product of Example 4 is applied and shaped onto the warm cast. The resin is shaped and flowed to fully cover the cast, using finger pressure and trimming to form a baseplate. The baseplate is cured for 10 minutes in the visible light curing unit. A sufficient quantity of the product of Example 6 is formed into a rope. The rope is applied to the baseplate. Then artificial teeth are pressed into the rope with the thickness of the rope adapted to adequately cover the appropriate surfaces of the teeth to provide support. Melted product of Example 5 from an about 87° C. wax pot is applied by using an electric spatula between the teeth and the baseplate to fully embed teeth and to flow into fissures between teeth and to smooth the outer surface of the denture. Hot air from a small nozzle hot air gun may also be applied to let the product of Example 5 flow into fissures between teeth and smooth the outer surface of the denture. The lingual and buccal surfaces of the denture are contoured, trimmed and carved using a spatula. The denture is placed in a patient's mouth for try-in at a dental office and tooth positions are adjusted. The denture back is fitted to the cast and the TRIAD Air Barrier Coating is painted on the denture. Then a model release agent (MRA) sold by Dentsply International Inc. is applied to around posterior teeth and supporting resin. A strip of Triad gel is applied on surface between teeth and supporting resin to form a continuous circle and cured in a visible light curing unit for 10 minutes, followed by post curing for 8 hours of gradually cooling to 23° C. When cured, the denture is washed with water to remove all traces of Air Barrier Coating. The denture is then finished and polished.

EXAMPLE 8

Preparation of a Partial Denture without Forming a Mold Cavity (Investment) of a Denture Base A removable partial denture framework is fabricated. A separating medium is applied to a gypsum cast of the patient''s dentition. A sufficient quantity of the product of Example 4 is applied onto the edentulous areas of the cast and adapted with finger pressure or appropriate instruments. Excess material is trimmed with a hot spatula. A sufficient quantity of the product of Example 4 is adapted into the tissue side finish line of the partial denture framework. The framework is seated on the cast firmly, embedding the uncured material of Example 4. All rests and tissue stops are varnished as correctly positioned on the cast, indicating that the framework is fully seated. Excess material is removed and these baseplate areas are cured in the visible light curing unit. A rope of the product of Example 6 is adapted onto the precured baseplate/edentulous areas. The rope has a thickness sufficient to cover the ridge lap surfaces of the teeth to provide support for the teeth and to seat the teeth, which are then set up in the rope. A portion the product of Example 5 is applied between the teeth and the baseplate. A small nozzle hot air gun is used to melt the product of Example 5 so that it flows into the fissures between teeth as the outer surface smoothes. The lingual and buccal surfaces of the edentulous areas are contoured, trimmed and carved using an electric hot spatula, sharp tools and hot air gun. The partial denture wax-up is removed from the cast for try-in. The denture is placed in a patient's mouth for try-in at a dental office and tooth positions adjusted if needed. The partial denture is fitted to a modified cast (reduced soft tissue heights of contour). TRAID Air Barrier Coating is painted onto the denture. Then a mold release agent (MRA) sold by Dentsply International, Inc. is applied around the postierior teeth and supporting resin. A strip of triad gel is applied between teeth and on the surface of the supporting resin to form a continuous circle. The denture is then cured in the visible light curing unit for 10 minutes, followed by cooling over a 2 hour period to 23° C. When cured, the partial denture is washed with water to remove all traces of Air Barrier Coating. The partial denture is then finished and polished.

EXAMPLE 9

Preparation of a Night Guard without Forming a Mold Cavity of a Night Guard

A plaster cast of a patient's teeth is coated with a release agent. 20 grams of the product composition of Example 3 is applied over the release agent and warmed to 50° C. in an oven. The composition is shaped using finger pressure and trimming to form a night guard which hardens when cooling to room temperature. The surfaces of the night guard are contoured, trimmed and carved using an electric hot spatula and hot air gun. After the night guard is examined and adjusted to fit articulator, the night guard is fitted to the cast and a TRAID Air Barrier Coating is painted on the denture and cured for 10 minutes. The clear night guard is then washed with water to remove all traces of Air Barrier Coating. The night guard is then finished and polished.

Example 7B of U.S. Pat. No. 6,057,383 (and Canadian Patent Application 2207351) was followed and the polymeric product thereof was tested to provide the information in the following Table. The polymerizable wax-like material of the present invention made by following the procedure of Example 5 was polymerized and the polymeric product was tested to provide the information in the following Table. Comparing the test results, Example 5's flexural strength is more than 500 percent greater than that of the tested material of U.S. Pat. No. 6,057,383. Example 5 of the present invention has a flexural modulus which is more than two times greater than that of the polymerizable wax-like material of U.S. Pat. No. 6,057,383. Example 5 of the present invention has an un-notched Impact Strength which is more than eight times greater than that of the polymerizable wax-like material of U.S. Pat. No. 6,057,383. Example 5 of the present invention has a notched Impact Strength which is more than two times greater than that of the polymerizable wax-like material of U.S. Pat. No. 6,057,383. Overall results show that the material of the invention is suitable for making a denture while the flexural strength and un-notched impact strength of the comparative examples are insufficient.

[t1]

TABLE

COMPARISON OF POLYMERIZABLE WAX-LIKE MATERIALS

| | Flexural strength (psi) | Flexural Modulus (kpsi) | Un-notched Impact Strength (ft-lbf/in) | Notched Impact Strength (ft-lbf/in$^2$) |
|---|---|---|---|---|
| U.S. Pat. No. 6,057,383 (Ivoclar) Example 7B | 2897 | 207.9 | 0.51 | 0.53 |
| Example 5 of the present invention | 16820 | 446.5 | 4.45 | 1.28 |

It should be understood that while the present invention has been described in considerable detail with respect to certain specific embodiments thereof, it should not be considered limited to such embodiments but may be used in other ways without departure from the spirit of the invention and the scope of the appended claims.

The invention claimed is:

1. A method of making a dental product, comprising:
providing a light curable material comprising a polymerizable urethane compound formed by a process comprising reacting a diol compound with a diisocyanate compound,
forming said light curable material, and
polymerizing said light curable material to form a dental product comprising high strength dental polymeric material having an un-notched impact strength of at least 4 foot-pound/inch$^2$, a flexural modulus of at least 350,000 psi and a flexural strength of at least 7,000 psi.

2. The method of claim 1 wherein said light curable material comprises a polymerizable urethane compound having a structure within the scope of the general formula:

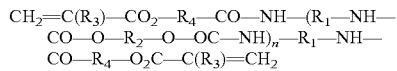

wherein $R_1$ and $R_2$ each independently is an alkyl having from 1 to 14 carbon atoms or an aromatic group having from 6 to 14 carbon atoms, $R_3$ is hydrogen, or an alkyl, and $R_4$ is an alkyl having from 1 to 14 carbon atoms, and n is an integer up to 20.

3. The method of claim 1 further comprising:
providing a cast of a patient,
forming said light curable material on said cast.

4. The method of claim 1 wherein said polymeric material a flexural modulus of at least 400,000 psi and a flexural strength of at least 12,000 psi.

5. The method of claim 1 wherein said dental product is a denture.

6. The method of claim 1 wherein said dental product is a full denture, partial denture, night guard or bridge.

7. The method of claim 1 wherein said cast has a shape selected from the group consisting of said patient's mouth and said patient's teeth.

8. The method of claim 1 wherein said polymerizable urethane compound is form from an isocyanate end-capped intermediate.

9. The method of claim 1 wherein said polymerizable urethane compound is formed from a viscous paste-like diisocyanate end-capped intermediate.

10. The method of claim 1 wherein said diisocyanate compound has a structure within the scope of the general formula:

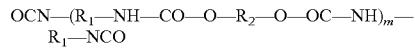

wherein $R_1$ and $R_2$ are alkyl having from 1 to 14 carbon atoms or an aromatic group having from 6 to 14 carbon atoms, m is an integer up to 20.

11. The method of claim 1 wherein said diol compound and said diisocyanate compound form an intermediate compound having a structure within the scope of a general formula selected from the group consisting of:

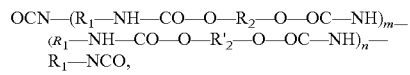

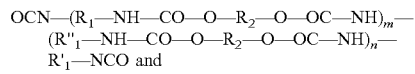

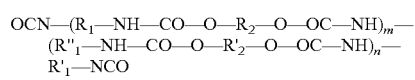

wherein $R_1$ and $R_2$ each independently is an alkyl having from 1 to 14 carbon atoms or an aromatic group having from 6 to 14 carbon atoms, and n is an integer up to 20.

12. The method of claim 1 wherein said urethane compound is formed from a isocyanate end-capped intermediate and a hydroxylalkymethacrylate.

13. The method of claim 1 wherein said diisocyanate is trimethyl-1,6-diisocyanatohexane, and said diol is bisphenol A propoxylate.

14. The method of claim 1 wherein said high strength dental polymeric material has an un-notched impact strength of at least 4.4 foot-pound/inch$^2$.

15. The method of claim 1 wherein said urethane compound is formed from trimethyl-1,6-diisocyanatohexane, bisphenol A propoxylate and 2-hydroxyethyl methacrylate.

16. The method of claim 1 wherein said polymerizable urethane compound has an aromatic group.

* * * * *